United States Patent
Whitehurst et al.

(10) Patent No.: US 6,650,943 B1
(45) Date of Patent: Nov. 18, 2003

(54) FULLY IMPLANTABLE NEUROSTIMULATOR FOR CAVERNOUS NERVE STIMULATION AS A THERAPY FOR ERECTILE DYSFUNCTION AND OTHER SEXUAL DYSFUNCTION

(75) Inventors: Todd K. Whitehurst, Sherman Oaks, CA (US); James P. McGivern, Stevenson Ranch, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 274 days.

(21) Appl. No.: 09/799,988

(22) Filed: Mar. 6, 2001

Related U.S. Application Data
(60) Provisional application No. 60/195,533, filed on Apr. 7, 2000.

(51) Int. Cl.$^7$ ................................................ A61N 1/36
(52) U.S. Cl. .......................................... 607/39; 607/72
(58) Field of Search ............................ 607/2, 72, 60, 607/118, 15–24, 39–59; 128/901

(56) References Cited

U.S. PATENT DOCUMENTS

| | | | |
|---|---|---|---|
| 3,941,136 A | | 3/1976 | Bucalo ........................ 128/422 |
| 4,167,466 A | * | 9/1979 | Orr, Jr. et al. ............... 204/176 |
| 4,542,753 A | | 9/1985 | Brenman et al. ........... 128/788 |

(List continued on next page.)

FOREIGN PATENT DOCUMENTS

| | | |
|---|---|---|
| WO | 9837926 | 3/1998 |
| WO | 9843700 | 8/1998 |
| WO | 9843701 | 8/1998 |

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9 (Sep. 1997), pp. 781–790.

Lue, et al., "Electrostimulation and Penile Erection", Urol. Int. 40 (1985), pp. 60–64.

Martinez–Pineiro, et al., Rat Model for the Study of Penile Erection: Pharmacologic and Eletrical–Stimulation Parameters, Eur Urol 25 (1994), pp. 62–70.

Shafik, A., "Extrapelvic Cavernous Nerve Stimulation in Erectile Dysfunction", Andrologia 28 (May–Jun. 1996), pp. 151–156.

Stief, et al., "The Influence of Anterior Root Stimulation (S2) in Deafferented Spinal Cord Injury Men on Cavernous Electrical Activity", The Journal of Urology 148 (Jul. 1992), pp. 107–110.

(List continued on next page.)

*Primary Examiner*—Mark Paschall
(74) *Attorney, Agent, or Firm*—Laura Haburay Bishop; Bryant R. Gold

(57) ABSTRACT

An implantable stimulator(s) with at least two electrodes, which is small enough to have the electrodes located adjacent to a cavernous nerve(s) or other nerve(s) innervating the reproductive organs, uses a power source/storage device, such as a rechargeable battery. Periodic recharging of such a battery is accomplished, for example, by inductive coupling with an external appliance. The small stimulator provides means of stimulating a nerve(s) when desired, without the need for external appliances during the stimulation session. When necessary, external appliances are used for the transmission of data to and/or from the stimulator(s) and for the transmission of power. In a preferred embodiment, the system is capable of open-and closed-loop operation. In closed-loop operation, at least one implant includes a sensor, and the sensed condition is used to adjust stimulation parameters.

24 Claims, 3 Drawing Sheets

U.S. PATENT DOCUMENTS

| | | | |
|---|---|---|---|
| 4,585,005 A | | 4/1986 | Lue et al. .................... 128/419 |
| 4,954,321 A | * | 9/1990 | Jenren .................... 422/186.19 |
| 5,193,539 A | | 3/1993 | Schulman et al. .......... 128/419 |
| 5,193,540 A | | 3/1993 | Schulman et al. .......... 128/419 |
| 5,312,439 A | | 5/1994 | Loeb ............................ 607/2 |
| 5,439,938 A | | 8/1995 | Snyder et al. .............. 514/565 |
| 5,454,840 A | | 10/1995 | Krakovsky et al. ........... 607/39 |
| 5,571,118 A | | 11/1996 | Boutos ....................... 607/138 |
| 5,756,054 A | * | 5/1998 | Wong et al. ........... 422/186.08 |
| 5,775,331 A | | 7/1998 | Raymond et al. ........... 128/741 |
| 5,938,584 A | | 8/1999 | Ardito et al. ................. 600/38 |
| 5,977,715 A | * | 11/1999 | Li et al. .................. 315/111.51 |
| 6,051,017 A | | 4/2000 | Loeb et al. ..................... 607/1 |
| 6,169,924 B1 | | 1/2001 | Meloy et al. ................. 607/39 |

OTHER PUBLICATIONS

Tai, et al., "Penile Erection Produced by Microstimulation of the Sacral Spinal Cord of the Cat", IEEE Transactions Rehabilitation Engineering 6 (Dec. 1998) pp. 374–381.

Shafik A., "Perineal Nerve Stimulation: Role in Penile Erection", International Journal of Impotence Research. 9 (Mar. 1997), pp. 11–16.

Shafik A., "Cavernous Nerve Stimulation Through an Extrapelvic Subpubic Approach: Role in Penile Erection", Eur Urol 26 (1994), pp. 98–102.

Creasey GH., "Electrical Stimulation of Sacral Roots for Micturition After Spinal Cord Injury", Urologic Clinics of North America 20 (Aug. 1993), pp. 505–515.

* cited by examiner

FULLY IMPLANTABLE NEUROSTIMULATOR FOR CAVERNOUS NERVE STIMULATION AS A THERAPY FOR ERECTILE DYSFUNCTION AND OTHER SEXUAL DYSFUNCTION

The present application claims the benefit of U.S. Provisional Patent Application Serial No. 60/195,533, filed Apr. 7, 2000, which application is incorporated herein by reference in its entirety.

FIELD OF THE INVENTION

The present invention generally relates to implantable stimulator systems, and more particularly relates to an implantable stimulator system utilizing one or more implantable microstimulators as a therapy for erectile dysfunction.

BACKGROUND OF THE INVENTION

Recent estimates suggest that the number of U.S. men with erectile dysfunction may be near 10 to 20 million, and inclusion of individuals with partial erectile dysfunction increases the estimate to about 30 million. The male erectile response is initiated by the action of neurons, or nerve cells (i.e., neuronal action), and maintained by a complex interplay between events involving blood vessels (i.e., vascular events) and events involving the nervous system (i.e., neurological events).

The part of the nervous system that regulates involuntary action (e.g., the intestines, heart, glands) is called the autonomic nervous system. The autonomic nervous system is divided into two mutually antagonistic, physiologically and anatomically distinct systems: the sympathetic nervous system and the parasympathetic nervous system. The sympathetic nervous system originates in the thoracic and lumbar regions of the spinal cord, and in general, opposes the physiological affects of the parasympathetic nervous system. For instance, the sympathetic nervous system will tend to reduce digestive secretions or speed up the heart, usually when an individual is in an active state. The parasympathetic nervous system originates in the brain stem and the lower part of the spinal cord, and, in general, opposes the physiological effects of the sympathetic nervous system. Thus, the parasympathetic nervous system will tend to stimulate digestive secretions or slow the heart usually when an individual is in a relaxed state.

It is parasympathetic neuronal action that initiates the male erectile response. Specifically, this parasympathetic input originates from the nerve plexus (i.e., a structure in the form of a network) called the pelvic splanchnic nerve plexus. The pelvic splanchnic nerve plexus is comprised of branches from the second, third, and fourth sacral nerves (from the lower part of the spinal cord) that intertwine with the inferior hypogastric plexus, which is a network of nerves in the pelvis. The cavernous nerves (designated greater and lesser) are derived from the pelvic splanchnic nerves, and supply parasympathetic fibers to the corpora cavernosum and corpus spongiosum, the erectile tissue in the penis containing large interspaces capable of being distended with blood.

This activity allows erection by relaxation of smooth muscle (i.e., muscle found in the walls of internal organs, blood vessels, hair follicles, etc. that contracts without voluntary control) and dilation of the helicine arteries, which are coiled arteries found in the erectile tissue of the penis. The dilation of the arteries causes greatly increased blood flow through the erectile tissue, which leads to expansion of the three cylinders of erectile tissue in the penis (i.e., the corpora cavernosum and the corpus spongiosum). As the corpora cavernosum and the corpus spongiosum expand, the venous structures draining the penis are compressed against the fascia surrounding each of the erectile tissues (i.e., the tunica albuginea of the corpora cavernosum and the tunica albuginea of the corpus spongiosum). Thus, the outflow of blood is restricted, and the internal pressure increases. This vein-obstruction process is referred to as the corporal veno-occlusive mechanism.

Conversely, constriction of the smooth muscle and helicine arteries induced by sympathetic innervation (i.e., stimulation by nerves) from the hypogastric nerves, for example, from certain nerves of the inferior hypogastric plexus, may make the penis flaccid.

Erectile dysfunction has a number of causes, both physiological and psychological, and in many patients the disorder may be multifactorial. The causes include several that are essentially neurologic in origin. Damage to the pathways used by the autonomic nervous system to innervate the penis may interrupt "psychogenic" erection initiated by the central nervous system. Psychogenic erection has a mental or emotional origin, rather than a physical basis. Lesions (e.g., injury, infection, or disease) of the somatic nervous pathways (i.e., any of the nerves associated with sensation or motion) may impair reflexogenic erections (i.e., involuntary, instinctive physiological response to a stimulus) and may interrupt tactile sensation needed to maintain psychogenic erections. Spinal cord lesions may produce varying degrees of erectile failure depending on the location and severity of the lesions.

Not only lesions affect erectile ability; disorders leading to peripheral neuropathy may also impair neuronal innervation of the penis. Peripheral neuropathy is a disorder or abnormality of the part of the nervous system constituting the nerves outside the central nervous system and including the cranial nerves, the spinal nerves, and the sympathetic and parasympathetic nervous systems. Peripheral neuropathy may also impair neuronal innervation of the sensory afferents—the nerves that conduct impulses from the periphery of the body to the brain or spinal cord, transmitting impulses from sense organs to nerve centers. Peripheral neuropathy is a potential sequela of a number of diseases, e.g., diabetes mellitus.

The endocrine system (glands such as the thyroid, adrenal, or pituitary, having hormonal secretions that pass directly into the bloodstream), particularly the production of androgens (steroid hormones, such as testosterone or androsterone, that control the development and maintenance of masculine characteristics), appears to play a role in regulating sexual interest, and may also play a role in erectile function.

In men of all ages, erectile failure may diminish willingness to initiate sexual relationships because of fear of inadequate sexual performance or rejection. Because males, especially older males, are particularly sensitive to the social support of intimate relationships, withdrawal from these relationships because of such fears may have a negative effect on their overall health.

Some forms of erectile dysfunction are currently treated with medication, with varying degrees of success. For instance, the well-publicized oral medication VIAGRA® (active ingredient sildenafil citrate) requires an hour to exert its full effects, and it may have significant side effects such as abnormal vision, flushing, headache, and diarrhea.

Intracavernosal injection therapy, in which a patient injects vasodilator substances (e.g., papaverine) into the corpora of the penis, suffers a high rate of patient dropout, as does the therapeutic application of vacuum constriction devices. Several forms of penile prostheses are available, including semirigid, malleable, and inflatable, but these have significant problems with mechanical failure, infection, and device erosion.

Various stimulation devices have been proposed for treating erectile dysfunction. Some devices stimulate through the skin, such as intrarectal stimulation devices. Other devices require significant surgical procedures for placement of electrodes, leads, and processing units. These devices may also require an external apparatus that needs to be strapped or otherwise affixed to the skin. While several patents exist regarding stimulators for treatment of erectile dysfunction, the inventors know of no chronic, fully implantable neurostimulator device that is commercially available.

BRIEF SUMMARY OF THE INVENTION

The invention disclosed and claimed herein provides means for chronically stimulating nerves derived from the pelvic splanchnic plexus, such as the cavernous nerves, with a miniature implantable neurostimulator that can be implanted with a minimal surgical procedure. Prior research suggests that stimulation of the cavernous nerve(s) may be an effective therapy for erectile dysfunction.

The cavernous nerves are relatively accessible as they run subcutaneously at the base of the dorsal penis. To treat erectile dysfunction, a miniature implantable neurostimulator, such as a Bionic Neuron (also referred to as a BION™ microstimulator) may be implanted adjacent to the cavernous nerves via a minimal surgical procedure (e.g., injection or small incision). A microstimulator may be implanted via injection and/or via endoscopic means. A more complicated surgical procedure may be required for sufficient access to a nerve or portion of a nerve (e.g., nerve fibers surrounded by scar tissue) or for purposes of fixing the neurostimulator in place.

A single microstimulator may be implanted, or two or more microstimulators may be implanted to achieve greater stimulation of the nerve fibers (e.g., all branches of the greater and lesser cavernous nerves). Alternatively, a microstimulator(s) may be implanted adjacent to parasympathetic targets deeper in the patient's body, such as the proximal cavernous nerves, the prostatic plexus, the pelvic splanchnic nerves, or the second, third, and/or fourth sacral nerves (i.e., S2, S3, S4). In order to inhibit sympathetic input that, e.g., retards erection, a microstimulator(s) may also/instead be implanted adjacent to the hypogastric nerve, certain nerves of the inferior hypogastric plexus or its branches, or the sympathetic ganglia from which the hypogastric nerve is derived.

Stimulation and control parameters of the implanted microstimulator are preferably adjusted to levels that are safe and efficacious with minimal discomfort. Different stimulation parameters have different effects on neural tissue, and parameters may be chosen to target specific neural populations and to exclude others. For example, relatively low frequency neurostimulation (i.e., less than about 50–100 Hz) may have an excitatory effect on surrounding neural tissue, leading to increased neural activity, whereas relatively high frequency neurostimulation (i.e., greater than about 50–100 Hz) may have an inhibitory effect, leading to decreased neural activity.

According to one embodiment of the invention, the stimulation can increase excitement of the parasympathetic input to, e.g., the penis; low-frequency electrical stimulation of parasympathetic fibers is likely to produce such excitement. According to another embodiment of the invention, the stimulation can decrease excitement of the sympathetic input to, e.g., the penis; high-frequency electrical stimulation of sympathetic fibers is likely to produce such inhibition.

The neurostimulator also includes means of stimulating nerve fibers either intermittently or continuously. Specific stimulation parameters may provide therapeutic advantages for various forms of erectile or other sexual dysfunction. Additional uses include the applications to emission (discharge of semen), ejaculation (ejection of semen in orgasm), and female sexual dysfunction.

It should be noted that the present invention is not directed to the "microstimulator", per se, which is the subject of other patents and patent applications, but is rather directed to methods of using the microstimulator, or a group of microstimulators, to treat erectile and other sexual dysfunction. However, the microstimulator used with the present invention preferably possesses one or more of the following properties:

at least two electrodes for applying stimulating current to surrounding tissue;

electronic and/or mechanical components encapsulated in a hermetic package made from biocompatible material (s);

an electrical coil inside the package that receives power and/or data by inductive or radio-frequency (RF) coupling to a transmitting coil placed outside the body, avoiding the need for electrical leads to connect devices to a central implanted or external controller;

means for receiving and/or transmitting signals via telemetry;

means for receiving and/or storing electrical power within the microstimulator; and a form factor making the microstimulator implantable via a minimal surgical procedure.

The power source of the microstimulator is preferably realized using one or more of the following options:

(1) an external power source coupled to the microstimulator via an RF link;

(2) a self-contained power source made using any means of generation and/or storage of energy, e.g., a primary battery, a replenishable or rechargeable battery, a capacitor, a supercapacitor; and/or (3) if the self-contained power source is replenishable or rechargeable, means of replenishing or recharging the power source, e.g., an RF link, an optical link, or other energy-coupling link.

A microstimulator may operate independently, or in a coordinated manner with other implanted devices, or with external devices. In addition, a microstimulator may incorporate means for sensing erectile or other sexual dysfunction, which it may then use to control stimulation parameters in a closed loop manner. According to one embodiment of the invention, the sensing and stimulating means are incorporated into a single microstimulator. According to another embodiment of the invention, a sensing means communicates sensed information to at least one microstimulator with stimulating means.

Thus, the present invention provides a therapy for erectile and other sexual dysfunction that utilizes one or more miniature neurostimulators and is minimally invasive. The simple implant procedure results in reduced surgical time and possible error, with associated advantages in terms of reduced expense and opportunity for infection or other complications. Other advantages, inter alia, of the present invention the system's monitoring and programming capabilities, the power source, storage, and transfer mechanisms, the activation of the device by the patient or clinician, the system's open and closed-loop capabilities and closed-loop capabilities coupled with sensing a need for and/or response to treatment, coordinated use of one or more stimulators, and the small size of the stimulator.

BRIEF DESCRIPTION OF THE DRAWINGS

The above and other aspects, features, and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
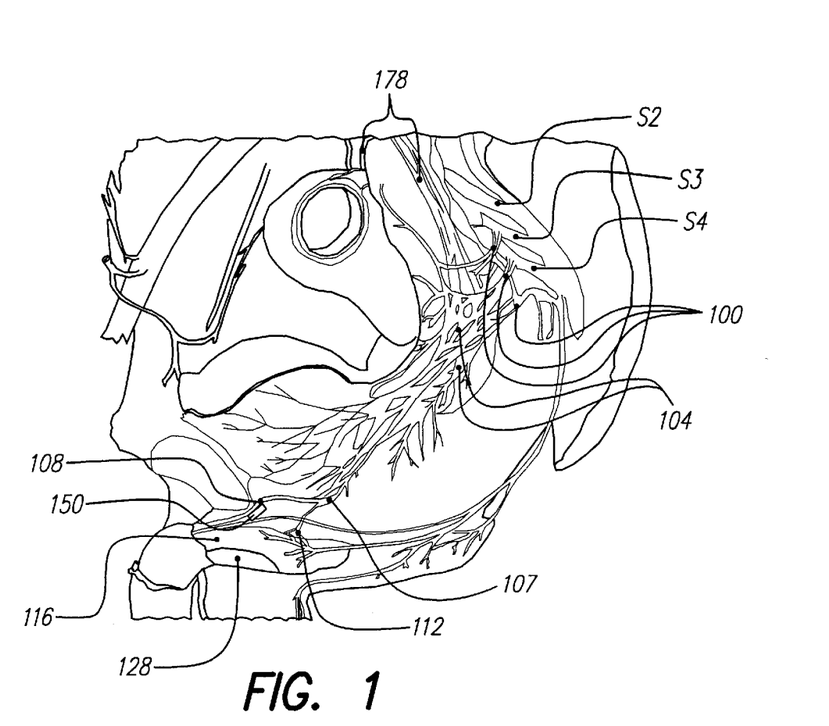
FIG. 1 depicts the nerves of the male pelvic viscera and surrounding anatomy, where a stimulation system of the present invention may be implanted.
Figure 2:
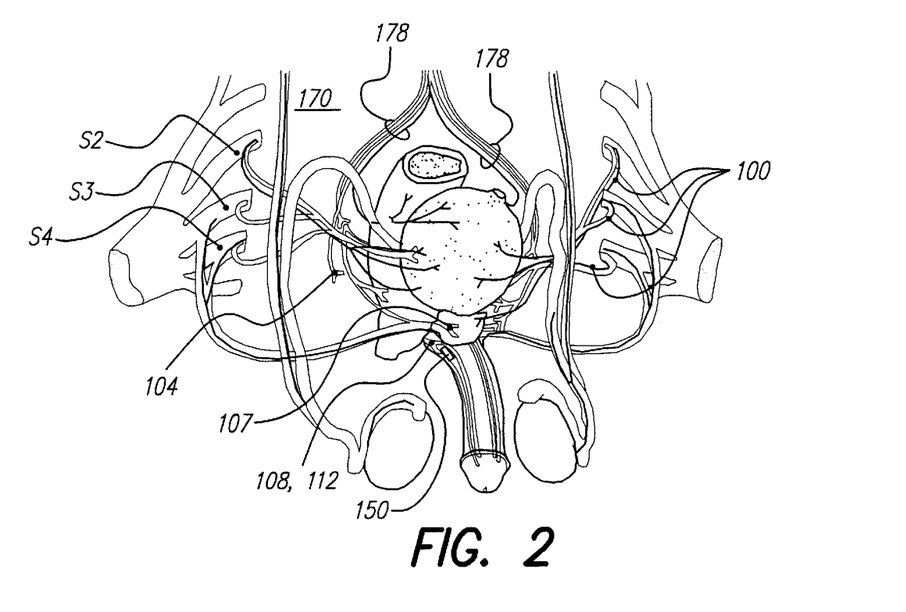
FIG. 2 illustrates the innervation of the male reproductive organs and a stimulation system of the present invention.

FIG. 1 depicts the nerves of a male pelvis, and FIG. 2 is a schematic representation of the sympathetic and parasympathetic fibers of the autonomic nervous system that are responsible for innervation of the male reproductive organs. The parasympathetic input that initiates the male erectile response originates in the pelvic splanchnic nerve plexus. The pelvic splanchnic nerves 100 are comprised of parasympathetic branches from the second, third, and fourth sacral nerves (S2, S3, S4, respectively) that intertwine with the inferior hypogastric plexus 104. Greater cavernous nerve 108 and lesser cavernous nerve 112 are derived from the pelvic splanchnic nerves, and carry the parasympathetic input to the corpora cavernosum 116 and corpus spongiosum 128.

Figure 3:
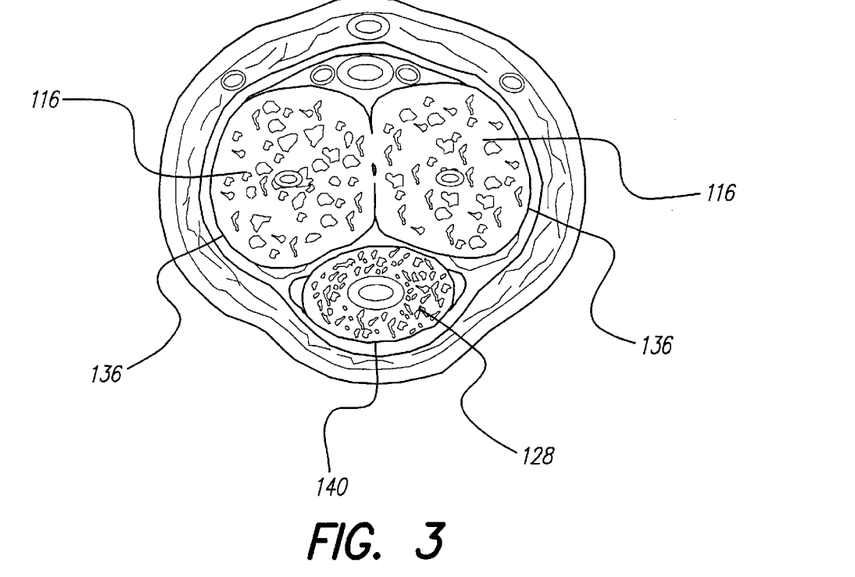
FIG. 3 is a section view through the body of a penis.

Referring next to FIG. 3, the parasympathetic signals carried to the corpora cavernosum 1 16 and corpus spongiosum 128 cause relaxation of smooth muscle surrounding the arteries and arterioles of the penis and dilation of the arteries and arterioles of the penis. The dilation of the arteries and arterioles causes increased blood flow through the erectile tissue, which leads to expansion of the corpora cavernosum 116 and the corpus spongiosum 128. Due to this expansion, the venous structures draining the penis are compressed against the corpora cavernosum's tunica albuginea 136 and the corpus spongiosum's tunica albuginea 140. Thus, the outflow of blood is restricted, and the internal pressure increases.

As indicated above, the present invention is directed to a method for treating erectile dysfunction or other sexual dysfunction using one or more implantable microstimulators. The microstimulators of the present invention are preferably of the type referred to as BION™ devices. The following documents describe various features and details associated with the manufacture, operation, and use of BION implantable microstimulators, and are all incorporated herein by reference:

| Application/Patent/ Publication No. | Filing/Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| PCT Publication WO 98/37926 | published Sept. 3, 1998 | Battery-Powered Patient Implantable Device |
| PCT Publication WO 98/43700 | published Oct. 8, 1998 | System of Implantable Devices For Monitoring and/or Affecting Body Parameters |
| PCT Publication WO 98/43701 | published Oct. 8, 1998 | System of Implantable Devices For Monitoring and/or Affecting Body Parameters |
| U.S. Pat. No. 6,054,017 | Issued Apr. 18, 2000 | Improved Implantable Microstimulator and Systems Employing Same |
| | published Sept. 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

Figure 4:
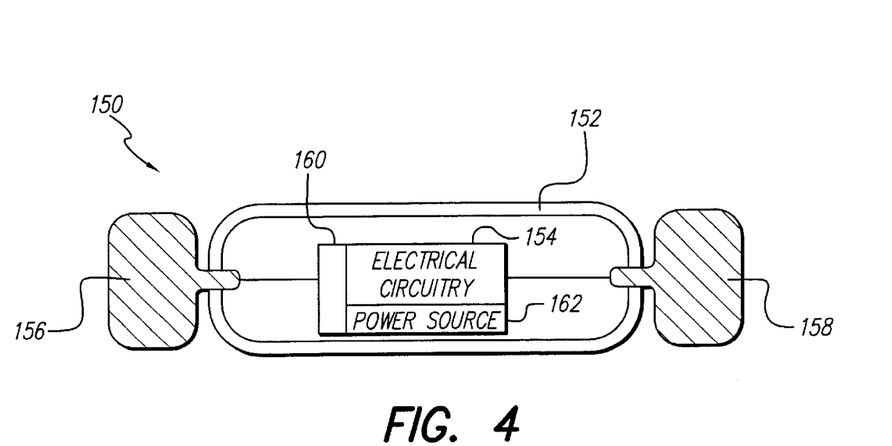
FIG. 4 illustrates an exemplary embodiment of a stimulation system of the present invention.

To treat erectile dysfunction, a microminiature stimulator 150, such as a BION microstimulator, illustrated, e.g., in FIG. 4, is preferably implanted adjacent to one or both cavernous nerves 108 and 112. Device 150 includes a narrow, elongated capsule 152 containing electronic circuitry 154 connected to electrodes 156 and 158, which pass through the walls of the capsule at either end. As detailed in the referenced patents, electrodes 156 and 158 comprise a stimulating electrode (to be placed close to the nerve) and an indifferent electrode (for completing the circuit). Other configurations of device 150 are possible, as is evident from the above-referenced patents.

Advantageously, implantable stimulator 150 is sufficiently small to permit its placement near the structures to be stimulated. As used herein, "adjacent" means as close as reasonably possible to the target nerve(s), including touching the target nerve(s), but in general, may be as far as about 150 mm from the target nerve(s). In accordance with the present invention, a single microstimulator 150 may be implanted, or two or more microstimulators may be implanted to achieve greater stimulation of all targeted nerve fibers (e.g., all branches of the greater and lesser cavernous nerves).

Capsule 152 preferably has a diameter no greater than about 4–5 mm, more preferably only about 3.5 mm, and most preferably less than 3.5 mm. Capsule length is preferably no greater than about 30–40 mm, more preferably only about 20–30 mm, and most preferably less than 20 mm. The shape of the microstimulator is preferably determined by the structure of the desired target, the surrounding area, and the method of surgical insertion. A thin, elongated cylinder with electrodes at the ends, as shown in FIG. 4, is currently preferred, but other shapes, such as disks or helical structures, are possible.

Microstimulator 150 is preferably implanted with a surgical insertion tool specially designed for the purpose, or is injected (e.g., via a hypodermic needle).

Alternatively, device 150 may be implanted via conventional surgical methods, or may be inserted using other endoscopic or laparoscopic techniques. A more complicated surgical procedure may be required for purposes of fixing the neurostimulator in place.

The external surfaces of stimulator 150 are advantageously composed of biocompatible materials. Capsule 152 is preferably made of glass or ceramic to provide a hermetic package that will exclude water vapor but permit passage of electromagnetic fields used to transmit data and/or power. Electrodes 156 and 158 are preferably made of a noble or refractory metal, such as platinum, iridium, tantalum, titanium, niobium or their alloys, in order to avoid corrosion or electrolysis which could damage the surrounding tissues and the device.

In one preferred embodiment of the instant invention, microstimulator 150 comprises two, leadless electrodes. However, either or both electrodes 156 and 158 may alternatively be located at the ends of short, flexible leads as described in U.S. patent application Ser. No. 09/624,130, filed Jul. 24, 2000, which is incorporated herein by reference in its entirety. The use of such leads permits electrical stimulation to be directed more locally to a specific nerve structure a short distance from the surgical fixation of the bulk of the implantable stimulator 150, while allowing all elements of stimulator 150 to be located in a more surgically convenient site. This minimizes the distance traversed and the surgical planes crossed by the device and any lead(s). In a preferred embodiment, the leads are no longer than about 100–150 mm.

Microstimulator 150 preferably contains electronic circuitry 154 for receiving data and/or power from outside the body by inductive, radio-frequency, or other electromagnetic coupling. In a preferred embodiment, electronic circuitry 154 includes an inductive coil for receiving and transmitting radio frequency (RF) data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), etc.

Neurostimulator 150 advantageously includes a programmable memory 160 for storing a set(s) of stimulation and control parameters. This feature allows electrical stimulation to be adjusted to settings that are safe and efficacious with minimal discomfort for each individual. Specific stimulation parameters provide therapeutic advantages for various forms of erectile dysfunction and other forms of sexual dysfunction. For instance, some patients may respond favorably to intermittent stimulation, while others require continuous stimulation to treat their dysfunction.

In addition, stimulation parameters may be chosen to target specific neural populations and to exclude others. For example, relatively low frequency neurostimulation (i.e., less than about 50–100 Hz) may have an excitatory effect on surrounding neural tissue, leading to increased neural activity, whereas relatively high frequency neurostimulation (i.e., greater than about 50–100 Hz) may have an inhibitory effect, leading to decreased neural activity.

The preferred implantable stimulator 150 also includes a power source and/or power storage device 162. Possible power options for a stimulation device of the present invention, described in more detail below, include but are not limited to an external power source coupled to stimulator 150 via an RF link, a self-contained power source utilizing any means of generation or storage of energy (e.g., a primary battery, a rechargeable battery such as a lithium ion battery, an electrolytic capacitor, or a super-or ultra-capacitor), and if the self-contained power source is replenishable or rechargeable, means of replenishing or recharging the power source (e.g., an RF link).

According to one embodiment of the invention, a microstimulator operates independently. According to another embodiment of the invention, a microstimulator operates in a coordinated manner with other microstimulator(s), other implanted device(s), or other device(s) external to the patient's body. For instance, a microstimulator may control or operate under the control of another implanted microstimulator(s), other implanted device(s), or other device(s) external to the patient's body. A microstimulator may communicate with other implanted microstimulators, other implanted devices, and/or devices external to a patient's body via, e.g., an RF link, an ultrasonic link, or an optical link. Specifically, a microstimulator may communicate with an external remote control (e.g., patient and/or physician programmer) that is capable of sending commands and/or data to a microstimulator and that is preferably capable of receiving commands and/or data from a microstimulator.

Figure 5:
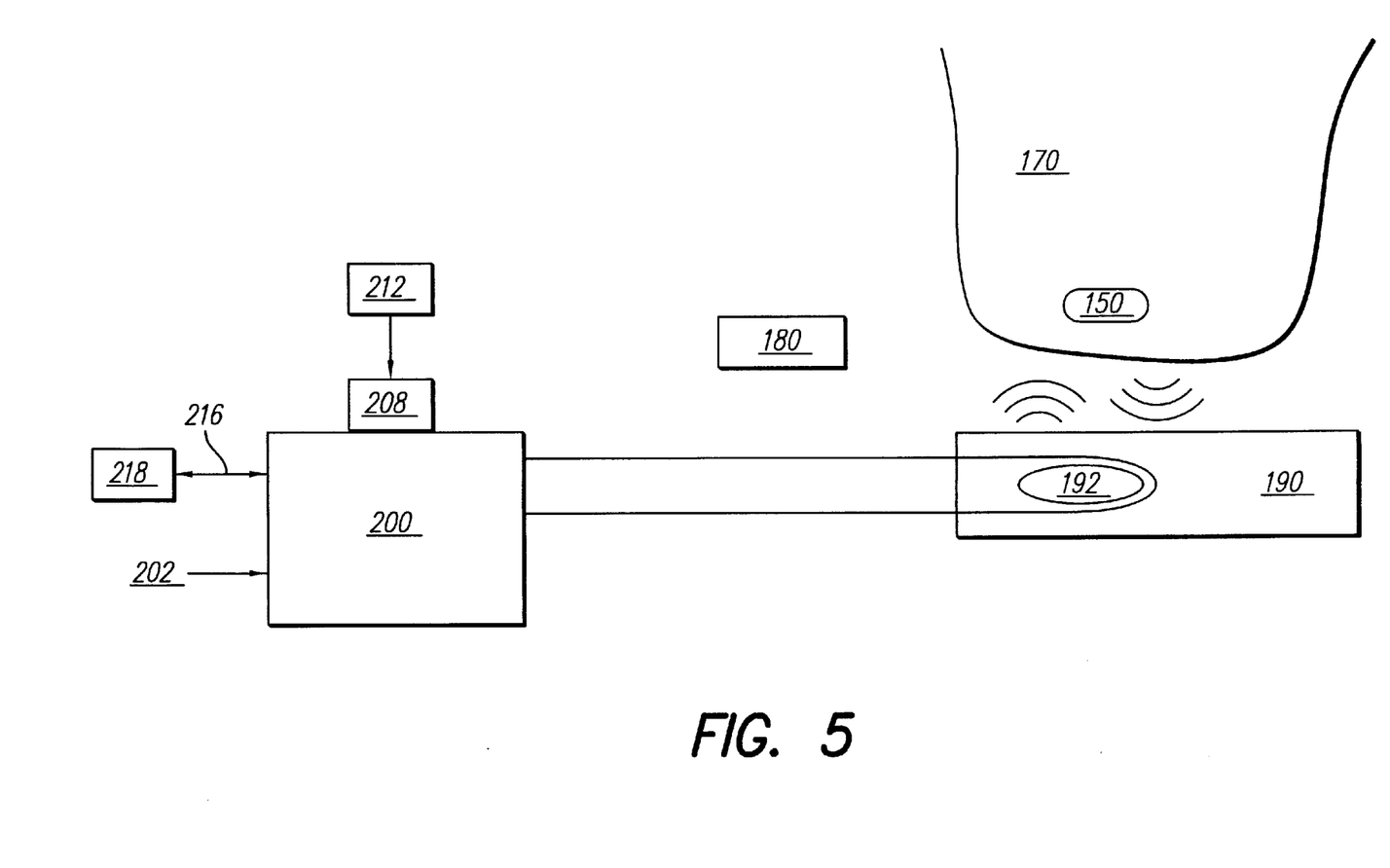
FIG. 5 illustrates external components of the invention.

In operation, as illustrated in FIG. 5, the patient 170 switches the implantable stimulator 150 on and off by use of controller 180, which is preferably handheld. Controller 180 operates to control the implantable stimulator 150 by any of various means, including sensing the proximity of a permanent magnet located in controller 180, or sensing RF transmissions from controller 180.

The external components related to programming and providing power to the implantable stimulator 150 are also illustrated in FIG. 5. When it is required to communicate with the implanted stimulator 150, the patient 170 is positioned on or near external appliance 190, which appliance contains one or more inductive coils 192 or other means of communication (e.g., RF transmitter and receiver). External appliance 190 is connected to or is a part of external electronic circuitry appliance 200 which receives power 202 from a conventional power source. External appliance 200 contains manual input means 208, e.g., a keypad, whereby the patient 170 or a caregiver 212 can request changes in the parameters of the stimulation produced during the normal operation of the implantable stimulator 150. In a preferred embodiment, the manual input means 208 includes various electromechanical switches and visual display devices that provide the patient and/or caregiver with information about the status and prior programming of the implantable stimulator 150.

Alternatively or additionally, the external electronic appliance 200 is preferably provided with an electronic interface means 216 for interacting with other computing means 218, such as by a serial interface cable or infrared link to a personal computer or to a telephone modem. Such interface means 216 thus permits a clinician to monitor the status of the implant and prescribe new stimulation parameters from a remote location.

The external appliance(s) may advantageously be embedded in a seat cushion, mattress cover, or garment. Other possibilities exist, including a belt or other structure that may be affixed to the patient's body or clothing.

In order to help determine the strength and duration of electrical stimulation required to produce the desired therapeutic effect, in one preferred embodiment, a patient's response to and/or need for treatment is sensed. For example, changes in penile arteriole pressure produced in response to stimulation may be sensed. Other measures of the state of the patient may additionally or alternatively be sensed, e.g., pressure in corpus cavernosum, pressure in corpus spongiosum, joint angle, muscle activity (e.g., EMG), nerve activity (e.g., ENG), hormone and/or enzyme levels or their changes, and/or levels or changes in level of other substance(s) borne in the blood.

For example, when implantable stimulator 150 is implanted adjacent to greater cavernous nerve 108, the signals from a pressure sensor built into microstimulator 150 may be recorded. Alternatively, a "microstimulator" dedicated to sensory processes communicates with a microstimulator that provides the stimulation pulses. The implant circuitry 154 amplifies and transmits these sensed signals, which may be analog or digital. Other methods of determining the required stimulation include observing the stimulation required to initiate erection, as well as other methods mentioned herein, and yet others that will be evident to those of skill in the art upon review of the present disclosure. The sensed information is preferably used to control the stimulation parameters of the stimulator in a closed-loop manner.

For instance, in one embodiment of the present invention, a first and second "stimulator" are provided. The second "stimulator" periodically (e.g. once per minute) records a level of muscle activity (or neural activity, etc.), which it transmits to the first stimulator. The first stimulator uses the sensed information to adjust stimulation parameters according to an algorithm programmed, e.g., by a physician. For example, the amplitude of stimulation may be increased in response to decreased penile arteriole pressure. More preferably, one stimulator performs both the sensing and stimulating functions.

While a microstimulator may also incorporate means of sensing dysfunction, it may alternatively or additionally be desirable to use a separate or specialized implantable device to record and telemeter physiological conditions/responses in order to adjust stimulation parameters. This information may then be transmitted to an external device, such as external appliance 190, or may be transmitted directly to implanted stimulator(s) 150. However, in some cases, it may not be necessary or desired to include a sensing function or device, in which case stimulation parameters are determined and refined, for instance, by patient feedback.

Thus, it is seen that in accordance with the present invention, one or more external appliances 200 may be provided to interact with microstimulator 150 to accomplish one or more of the following functions:

Function 1: If necessary, transmit electrical power from the external electronic appliance 200 via appliance 190 to the stimulator 150 in order to power the device and/or recharge the power source/storage device 162. External electronic appliance 200 may include an automatic algorithm that adjusts stimulation parameters automatically whenever the implantable stimulator(s) 150 is/are recharged.

Function 2: Transmit data from the external appliance 200 via the external appliance 190 to the implantable stimulator 150 in order to change the operational parameters (e.g., electrical stimulation parameters) produced by stimulator 150.

Function 3: Transmit sensed data indicating a need for treatment or in response to stimulation from neurostimulator 150 (e.g., impedance, pressure, joint angle, electromyographical activity, level of a blood-borne substance(s), or other activity) to external appliance 200 via the external appliance 190.

Function 4: Transmit data indicating state of the implantable stimulator 150 (e.g., battery level, stimulation settings, etc.) to external appliance 200 via external appliance 190.

By way of example, a treatment modality for erectile dysfunction is carried out according to the following sequence of procedures:

1. A stimulator 150 is implanted so that its electrodes 156 and 158 are adjacent to greater cavernous nerve 108. If necessary or desired, one or more additional stimulator(s) 150 may additionally or alternatively be implanted adjacent to other nerve fibers, such as the lesser cavernous nerve 112.

2. Using Function 2 described above (i.e., transmitting data) of external electronic appliance 200 and external appliance 190, implantable stimulator 150 is commanded to produce a series of electrical stimulation pulses with gradually increasing amplitude.

3. After each stimulation pulse, or brief series of stimulation pulses, or at some other predefined interval, any change in arteriole pressure in arteries supplying the penis (and/or intra-cavernosal pressure) is sensed, preferably by one or more electrodes 156 and 158 or sensors. These responses are converted to data and telemetered out to external electronic appliance 200 via Function 3.

4. From the response data received at external appliance 200 from the implantable stimulator 150, the stimulus threshold for obtaining a response is determined and is used by a clinician acting directly 212 or by other computing means 218 to transmit the desired stimulation parameters to the implantable stimulator 150 in accordance with Function 2.

5. When patient 170 desires to invoke an electrical stimulation to instigate erection, he employs controller 180 to set the implantable stimulator 150 in a state where it delivers a prescribed stimulation pattern from a predetermined range of allowable stimulation patterns.

6. To allow his penis to return to a flaccid state, patient 170 employs controller 180 to turn off stimulator 150.

7. Periodically, the patient or caregiver recharges the power source/storage device 162 of implantable stimulator 150 in accordance with Function 1 described above (i.e., transmit electrical power).

For the treatment of any of the various types of sexual dysfunction, it may be desirable to modify or adjust the algorithmic functions performed by the implanted and/or external components, as well as the surgical approaches, in ways that would be obvious to skilled practitioners of these arts. For example, it may be desirable to employ more than one implantable stimulator 150, each of which could be separately controlled by means of a digital address. Multiple channels and/or multiple patterns of stimulation might thereby be programmed by the clinician and controlled by the patient in order to deal with complex or multiple dysfunctions such as may occur as a result of spinal cord injury and neurodegenerative disorders.

In one preferred embodiment, microstimulator 150, or a group of two or more microstimulators, is controlled via closed-loop operation. A need for and/or response to stimulation is sensed via microstimulator 150, or by an additional microstimulator (which may or may not be dedicated to the sensing function), or by another implanted or external device. If necessary, the sensed information is transmitted to microstimulator 150. Preferably, the stimulation parameters used by microstimulator 150 are automatically adjusted based on the sensed information. Thus, the stimulation parameters are adjusted in a closed-loop manner to provide stimulation tailored to the response to stimulation.

According to one therapeutic alternative, the dysfunction may be treated with increased excitement of the parasympathetic input to the penis. Relatively low- frequency electrical stimulation (e.g., less than about 50–100 Hz) is likely to produce such excitement. Therefore, as described above, stimulation may be applied to one or more of the cavernous nerves. Alternatively or additionally, a stimulator(s) 150 may be implanted adjacent to parasympathetic targets deeper in the patient's body, such as the proximal portion of cavernous nerves 108 and 112, the prostatic plexus 107, the pelvic splanchnic nerves 100, or the second, third, and/or fourth sacral nerves (S2, S3, S4).

According to another therapeutic alternative, the dysfunction may be treated by inhibiting excitement of sympathetic nerve input to the penis. In this case, relatively high-frequency electrical stimulation (e.g., greater than about 50–100 Hz) is likely to produce such inhibition. Thus, a microstimulator(s) may also/instead be implanted adjacent to one or more of the hypogastric nerves 178, certain nerves of the inferior hypogastric plexus 104 or its branches, or the sympathetic ganglia from which they arise, in order to inhibit sympathetic input that retards erection.

In yet another alternative, placement of the microstimulator(s) may be chosen to effect emission (discharge of semen) or ejaculation (ejection of semen in orgasm). While parasympathetic input is responsible for erection, sympathetic impulses are required for ejaculation. As stated earlier, the sympathetic nervous system originates in the thoracic and lumbar regions of the spinal cord. It is believed that a portion of the sympathetic outflow leaving the spinal cord at the first and second lumbar segments travels through the lower lumbar or pelvic parts of the sympathetic trunk, then via the inferior hypogastric plexus, to arrive at the vas deferens, the seminal vesicles, and the prostate. Therefore, stimulating certain branches of the inferior hypogastric plexus that innervate the prostate, seminal vesicles, and vas deferens may lead to emission and/or ejaculation. Alternatively or additionally, stimulation of the pelvic splanchnic nerves leading to the prostate may cause emission and/or ejaculation.

Furthermore, sensing means described earlier may be used to orchestrate first the activation of microstimulator(s) targeting nerves that cause erection, and then, when appropriate, the microstimulator(s) targeting nerves that cause ejaculation. Alternatively, this orchestration may be programmed, and not based on a sensed condition.

By applying the methods of treatment taught herein to the analogous neuromuscular structures of the female anatomy (e.g., stimulating nerves of the uterovaginal plexus and branches thereof rather than the prostatic plexus and branches thereof), the treatment may be adapted for female sexual dysfunction, e.g., affecting clitoral engorgement, increased vaginal secretions, and/or treatment of vaginismus and/or dyspareunia.

While the invention herein disclosed has been described by means of specific embodiments and applications thereof, numerous modifications and variations could be made thereto by those skilled in the art without departing from the scope of the invention set forth in the claims.

What is claimed is:

1. A method for treating a patient with sexual dysfunction comprising:
   providing at least one leadless stimulator having at least two electrodes;
   implanting the at least one stimulator adjacent to at least one nerve innervating the reproductive organs;
   providing operating power to the at least one stimulator;
   using at least one external appliance to transmit stimulation parameters to the at least one stimulator;
   receiving and storing the stimulation parameters;
   generating stimulation pulses in accordance with the stimulation parameters; and
   delivering the stimulation pulses to nerve fibers adjacent to the at least one stimulator;
   wherein the stimulator has a size and shape suitable for placement of the electrodes adjacent to the at least one nerve innervating the reproductive organs.

2. The method of claim 1 wherein the at least one nerve supplies parasympathetic input to the reproductive organs and wherein the stimulation pulses are provided at less than about 50 to 100 Hz.

3. The method of claim 2 wherein the at least one nerve comprises at least one nerve of the cavernous nerves, the prostatic plexus, branches of the prostatic plexus, the uterovaginal plexus, branches of the uterovaginal plexus, the pelvic splanchnic nerves, the second, third, and fourth sacral nerves, the hypogastric nerves.

4. The method of claim 1 wherein the at least one nerve supplies sympathetic input to the reproductive organs and wherein the stimulation pulses are provided at greater than about 50 to 100 Hz.

5. The method of claim 4 wherein the at least one nerve comprises one or more of the sympathetic ganglia from which the hypogastric nerves arise, the hypogastric nerves, the nerves of the inferior hypogastric plexus, and the nerves of the branches of the inferior hypogastric plexus.

6. The method of claim 1 wherein the at least one nerve effects emission or ejaculation.

7. The method of claim 6 wherein the at least one nerve comprises at least one nerve of the branches of the inferior hypogastric plexus that innervate at least one of the prostate, seminal vesicles, and vas deferens.

8. The method of claim 6 wherein the at least one nerve comprises at least one of the pelvic splanchnic nerves leading to the prostate.

9. The method of claim 1 wherein the implantable stimulator further comprises at least one sensor.

10. The method of claim 9 wherein the sensed condition is used to adjust the stimulation parameters.

11. The method of claim 10 wherein the parameter adjustment is performed using the at least one external appliance.

12. The method of claim 10 wherein the parameter adjustment is performed by the implantable stimulator.

13. The method of claim 1 further comprising more than one implantable stimulator.

14. The method of claim 13 wherein at least one stimulator includes at least one sensor and wherein the sensed condition is used to adjust the stimulation parameters of at least one stimulator.

15. A method for treating a patient with at least one sexual dysfunction, comprising the steps of:
    providing at least one means for stimulating tissue;
    implanting the at least one stimulating means adjacent to at least one nerve innervating at least one reproductive organ;

providing operating power to the at least one stimulating means;

transmitting stimulation parameters to the at least one stimulating means using at least one external appliance;

receiving and storing the stimulation parameters;

generating stimulation pulses in accordance with the stimulation parameters; and delivering the stimulation pulses to nerves fibers adjacent to the at least one stimulating means;

wherein the stimulating means has a size and shape suitable for placement near the at least one nerve and has leads up to about 150 mm long.

16. The method of claim 15 wherein the body of the stimulator is no more than about 150 mm from the at least one nerve to be stimulated.

17. The method of claim 16 wherein the at least one nerve comprises one or more of the cavernous nerves, the nerves of the prostatic plexus, the nerves of the branches of the prostatic plexus, the nerves of the uterovaginal plexus, the nerves of the branches of the uterovaginal plexus, the pelvic splanchnic nerves, the second, third, and fourth sacral nerves, the hypogastric nerves, the sympathetic ganglia from which the hypogastric nerves arise, the hypogastric nerves, the nerves of the inferior hypogastric plexus, and the nerves of the branches of the inferior hypogastric plexus.

18. A method for treating a patient with at least one sexual dysfunction, comprising:

providing at least one leadless stimulator having at least two electrodes;

providing at least one sensor;

implanting the at least one stimulator adjacent to at least one nerve innervating at least one reproductive organ;

providing operating power to the at least one stimulator;

using the sensor to sense a physical condition;

determining stimulation parameters based upon the sensed condition;

generating stimulation pulses in accordance with the stimulation parameters; and delivering the stimulation pulses to nerve fibers adjacent to the at least two electrodes;

wherein the stimulator has a size and shape suitable for placement of the electrodes adjacent to the at least one nerve.

19. The method of claim 18 wherein the at least one sensor is a part of the stimulator.

20. The method of claim 18 wherein the stimulation parameters are determined using at least one external appliance.

21. The method of claim 18 wherein providing power to the at least one stimulator comprises receiving power from at least one external appliance.

22. The method of claim 21 wherein providing power to the at least one stimulator further comprises storing the power received from the at least one external appliance.

23. The method of claim 18 further comprising providing and implanting more than one stimulator.

24. The method of claim 18 wherein the at least one nerve comprises one or more of the cavernous nerves, the nerves of the prostatic plexus, the nerves of the branches of the prostatic plexus, the nerves of the uterovaginal plexus, the nerves of the branches of the uterovaginal plexus, the pelvic splanchnic nerves, the second, third, and fourth sacral nerves, the hypogastric nerves, the sympathetic ganglia from which the hypogastric nerves arise, the hypogastric nerves, the nerves of the inferior hypogastric plexus, and the nerves of the branches of the inferior hypogastric plexus.

* * * * *